United States Patent
Ott

(10) Patent No.: US 12,168,641 B2
(45) Date of Patent: Dec. 17, 2024

(54) PROCESS FOR THE PREPARATION OF HALOALKANESULFONIC ACIDS FROM SULFUR TRIOXIDE AND A HALOALKANE AT SUPERACIDIC CONDITIONS

(71) Applicant: GRILLO CHEMICALS GmbH, Duisburg (DE)

(72) Inventor: Timo Ott, Duisburg (DE)

(73) Assignee: GRILLO CHEMICALS GMBH, Duisburg (DE)

( * ) Notice: Subject to any disclaimer, the term of this patent is extended or adjusted under 35 U.S.C. 154(b) by 495 days.

(21) Appl. No.: 17/439,927

(22) PCT Filed: Mar. 17, 2020

(86) PCT No.: PCT/EP2020/057262
§ 371 (c)(1),
(2) Date: Sep. 16, 2021

(87) PCT Pub. No.: WO2020/187901
PCT Pub. Date: Sep. 24, 2020

(65) Prior Publication Data
US 2022/0153691 A1  May 19, 2022

(30) Foreign Application Priority Data
Mar. 21, 2019 (EP) .................................. 19164464

(51) Int. Cl.
*C07C 303/06* (2006.01)

(52) U.S. Cl.
CPC .................................. *C07C 303/06* (2013.01)

(58) Field of Classification Search
CPC .......................... C07C 303/06; C07C 309/06
See application file for complete search history.

(56) References Cited

FOREIGN PATENT DOCUMENTS

| WO | 2018096138 A1 | 5/2018 |
| WO | 2018146153 A1 | 8/2018 |

OTHER PUBLICATIONS

Mukhopadhya, s., et al., Wynthesis of trifluoromethanesulfonic acid form CHF3, Organic process research & development, vol. 8,No. 4, pp. 660-662 (Year: 2004).*
Mukhopadhyay, S., et al., "Synthesis of trifluoromethanesulfonic acid from CHF3", Organic Process Research & Development, Jun. 11, 2004, pp. 660-662, vol. 8, No. 4.
International Search Report and Written Opinion dated Jun. 3, 2020, prepared in International Application No. PCT/EP2020/057262.

* cited by examiner

*Primary Examiner* — Yate' K Cutliff
(74) *Attorney, Agent, or Firm* — Barnes & Thornburg LLP

(57) ABSTRACT

The present invention refers to a method for the production of haloalkane sulfonic acid, in which $SO_3$ and an haloalkane are contacted with each other in the presence of a solvent, said solvent does constitute a superacid and the combination of said solvent with one or more of the reactants also gives rise to a superacid.

18 Claims, No Drawings

PROCESS FOR THE PREPARATION OF HALOALKANESULFONIC ACIDS FROM SULFUR TRIOXIDE AND A HALOALKANE AT SUPERACIDIC CONDITIONS

This application is a U.S. National Stage application of International Application No. PCT/EP2020/057262, filed Mar. 17, 2020, the entire contents of which is hereby incorporated herein by reference. This application also claims the benefit under 35 U.S.C. § 119 of European Patent Application No. 19164464.0, filed Mar. 21, 2019, the entire contents of which is hereby incorporated herein by reference.

The present invention relates to a process for preparing haloalkanesulfonic acids from sulfur trioxide and a haloalkane, particularly to a process for preparing trifluoromethane sulfonic acid from sulfur trioxide and trifluoromethane, in which $SO_3$ and an haloalkane are contacted with each other in the presence of a solvent, said solvent does constitute a superacid and the combination of said solvent with one or more of the reactants also gives rise to a superacid.

Haloalkanes, also known as halogenalkanes or alkyl halides, are a group of chemical compounds structurally derived from alkanes by replacing one or more hydrogen atoms by halogen atoms. They are widely used as flame retardants, fire extinguishants, refrigerants, propellants, solvents and pharmaceuticals. By replacing a hydrogen atom of a haloalkane by a sulfonic acid group $SO_3H$, haloalkanesulfonic acids can be derived. Said haloalkanesulfonic acids are also formally derivable from alkanesulfonic acids by replacing hydrogen atoms by halogen atoms.

Among the haloalkanesulfonic acids, trifluoromethanesulfonic acid (TFMS), which is also known as triflic acid and has the chemical formula $CF_3SO_3H$, is of particular technical importance. At room temperature TFMS is a hygroscopic, clear and colorless liquid, soluble in polar solvents. Notably, TFMS is a super acid and with a pKa value of −14.7 one of the strongest known acids. Trifluoromethansulfonic acid is widely used as a catalyst for esterification, and isomerization, among other reactions. Triflic acid's conjugate base $CF_3SO_3-$ is called triflate and is a well-known protection group in organic chemistry. On an industrial scale, trifluoromethanesulfonic acid is particularly used in the polymer, fuel, pharmaceutical and sugar industry.

On an industrial scale, trifluoromethanesulfonic acid is produced by electrochemical fluorination of methanesulfonic acid (T. Gramstad and R. N. Haszeldine, J. Chem. Soc., 1956, 173). In theory, trifluoromethanesulfonic acid could also be prepared by the direct reaction of trifluoromethane ($CF_3H$) and sulfur trioxide.

$CF_3H$ is a strong greenhouse gas with a global warming potential of 15,000 times more than one molecule of carbon dioxide. It was formerly used as a refrigerant, although this application should now be avoided. Trifluoromethane is still produced, however, as an undesirable side-product in a number of industrial processes, e.g., in the production of polytetrafluoroethylene (PTFE), also known as teflon. There is thus need to eliminate excess trifluoromethane, preferably by transforming it into some useful and harmless substance. The reaction with sulfur trioxide might yield TFMS, which is considered to be an environmentally friendly acid.

Mukhopadhyay et al. (S. Mukhopadhyay, A. T. Bell, R. V. Srinivas, G. S. Smith, Org. Proc. Res. Dev. 2004, 8, 660) describe the direct synthesis of trifluoromethanesulfonic acid from trifluoromethane and sulfur trioxide employing hydrogen peroxide—urea and $RhCl_3$ as catalyst in fuming sulfuric acid. The yield, however, is small and the method is not economically feasible.

Therefore, there is still need for a process, which can transform trifluoromethane to trifluoromethanesulfonic acid in an efficient and economically feasible way. Such a process could provide both an efficient route to trifluoromethanesulfonic acid and a new method to eliminate trifluoromethane by converting it to a useful and harmless substance.

It is thus the object of the present invention to provide an improved process for the preparation of haloalkanesulfonic acids from the respective haloalkane and sulfur trioxide. Particularly, a process for the preparation of trifluoromethanesulfonic acid from trifluoromethane and sulfur trioxide should be provided.

Surprisingly, it was now found that stable reaction conditions can be obtained when working under superacid conditions. Thus, the solvent has to be selected extremely carefully. It was now found that selecting an appropriate solvent helps to provide improved reaction conditions. According to the classical definition, a superacid is an acid with an acidity greater than that of 100% pure sulfuric acid, which has a Hammett acidity function ($H_0$) of −12. According to the modern definition, a superacid is a medium in which the chemical potential of the proton is higher than in pure sulfuric acid. Consequently, the pKa value is negative.

In a first aspect, the present application therefore provides for a method for producing haloalkane sulfonic acids in which $SO_3$ and an haloalkane are contacted with each other in the presence of a solvent, wherein said solvent does constitute a superacid and/or the combination of said solvent with $SO_3$ and/or the haloalkane sulfonic acid does give rise to a superacid, with the proviso that the solvent is not $H_2SO_4$. In a preferred embodiment, $SO_3$ and haloalkane are contacted with each other in the presence of a compound being able to initialize the reaction between $SO_3$ and the haloalkane.

In the present case, the solvent alone or the combination of solvent and $SO_3$ or the combination of solvent and haloalkane sulfonic acid or the combination of solvent and $SO_3$ and haloalkane sulfonic acid constitutes a super acid, meaning that it has a pKa value of less than −3, i.e. the pKa value is more negative. The acidity is therefore of course higher.

In a preferred embodiment, the method is a method for the production of triflic acid.

In one preferred embodiment, the present invention provides for a method for manufacturing haloalkane sulfonic acids, especially triflic acid, comprising the following steps:
 a. Providing sulfur trioxide $SO_3$;
 b. Providing an haloalkane, especially trifluoromethane;
 c. Providing a solvent, wherein said solvent does constitute a superacid and the combination of said solvent with $SO_3$ and/or the haloalkane sulfonic acid does give rise to a superacid;
 d. Bringing into contact $SO_3$, haloalkane and the solvent in a high-pressure autoclave or laboratory reactor;
 e. Setting a pressure of from 1 to 200 bar;
 f. Adding a compound which is able to initialize the reaction between $SO_3$ and haloalkane at the described reaction conditions;
 g. Controlling the temperature of the reaction mixture at 0° C. to 100° C.;
 h. Letting react the compounds so that the haloalkane sulfonic acid, especially triflic acid, is formed,
with the proviso that the solvent is not $H_2SO_4$.

In the following, the present invention will be described in more detail. Features mentioned for one embodiment can be also used in other embodiments, even if not explicitly mentioned.

Surprisingly, it was found that superacid conditions provide for a direct sulfonation of an haloalkane, especially trifluoromethane, with $SO_3$. The speed of the reaction is dependent on the acidity of the reaction conditions. The stronger the acidity, the faster the reaction—without negatively influencing the purity of the obtained product.

The solvent according to the present invention is selected such that the solvent alone does constitute a super acid. It may be, that in the reactor, in which the educts and the solvent react with each other, the solvent and $SO_3$ react with each other in any kind, or interact with each other. Also, such a reaction or interaction of the solvent with $SO_3$ does give rise to a super acid according to the present invention. The same is true for the combination of the solvent and the haloalkane sulfonic acid which is formed during the reaction in the reactor. Thus, the solvent alone does constitute a super acid. Also or alternatively, the combination of the solvent and $SO_3$ does give rise to a super acid. Further, the combination of the solvent and the haloalkane sulfonic acid does give rise to super acid. Also the combination of the solvent with $SO_3$ and the haloalkane sulfonic acid does give rise to super acid within the meaning of the present invention. It is within the meaning of the present invention that as soon as either the solvent alone constitutes a super acid or the solvent in combination with $SO_3$ or the solvent in combination with haloalkane sulfonic acid or the solvent in combination with $SO_3$ and haloalkane sulfonic acid gives rise to a superacid, the solvent is within the scope of the present claims.

A super acid is an acid with an acid strength stronger than that of pure $H_2SO_4$. Therefore, in the meaning of the present invention a super acid means an acid with a pKa value less than −3.

The method of the present invention is suitable to produce different kinds of haloalkane sulfonic acids. Preferably, the haloalkane which is used as educt and from which the respective haloalkane sulfonic acid is formed, is a short chain haloalkane with 1 to 10 C atoms which can be linear or non-linear. Preferably, the haloalkane is an alkane with 1 to 5 C-atoms, wherein at least one, preferably at least two, particularly at least three H-atoms are replaced by a halogen. The halogen may be F, Cl, Br, I, especially it is F. It is within the meaning of the present invention that all H-atoms of the alkane a replaced by one or more halogens. Preferably, the haloalkane is trifluoromethane so that the haloalkane sulfonic acid being formed according to the method of the present invention is triflic acid.

The reaction between $SO_3$ and the haloalkane in the present solvent usually takes place in a high-pressure autoclave. Thus, the pressure at which $SO_3$ and haloalkane are contacted with each other is preferably in a range of from 1 bar to 200 bar, especially from 50 bar to 150 bar, preferably from 80 bar to 120 bar.

The temperature during the reaction is preferably within a range of from 0° C. to 100° C., especially from 15° C. to 80° C., especially preferred from 20° C. to 70° C., preferably from 35° C. to 60° C. In a preferred embodiment, the temperature at which $SO_3$ and haloalkane are contacted with each other is below 70° C., especially below 65° C., preferably below 60° C. and especially preferred below 55° C. If the temperature is around 0° C. or 10° C., the reaction time increases tremendously so that for an economically process the temperature is preferably 20° C. or above, especially 25° C. or above, especially preferred 30° C. or above.

If the preferred reaction conditions are used, the pressure being from 1 bar to 200 bar and the temperature is controlled to be between 0° C. to 100° C., the solvent used in a method according to the present invention is liquid under the respective conditions. Usually, $SO_3$ is provided as liquid so it is homogenously distributed in the solvent. The haloalkane is added either as a gas or as liquid depending on the length of the C chain. For haloalkanes with low boiling point, the use of a pressure reactor is therefore usually necessary. For pentane or higher haloalkanes, a common laboratory reactor is sufficient. In case of gaseous haloalkanes, for example trifluoromethane, a pressure of 1 bar to 100 bar is set.

At the interphase between liquid and gas or in the complete reactor in case of sufficient mixture of the reaction mixture the reaction takes place so that in the reactor remains a mixture of $SO_3$, haloalkane, solvent as well as the formed haloalkane sulfonic acid. Accordingly, at that this stage of the reaction, the conditions inside the reactor are super acid.

Solvents which preferably are used in the method of the present invention are selected from the group comprising fluoroantimonic acid, carborane acids, magic acid, fluorosulfuric acid, hydrogen fluoride, triflic acid, or mixtures of two or more of them. These solvents are all superacids. A solvent constituting superacid conditions within the meaning of the present invention is also a combination of two or more solvents, wherein a first solvent does not consconsitute a superacid, but a second solvent constituting a superacid is added to said first solvent and the combination of said first and said second solvent give rise to a superacid. Within the meaning of the present application is also a mixture of a first solvent and a second solvent, wherein the first solvent alone does not constitute a superacid and the second solvent alone does alo not constitute a superacid, but the mixture of said first acid and said second acid give rise to a superacid. Where a mixture of two solvents is mentioned, it is also within the scope of the present invention, that a mixture of three or more solvent is used.

Magic acid is a super acid consisting of a mixture most commonly in a 1:1 molar ratio, of fluorosulfuric acid ($HSO_3F$) and antimony pentafluoride ($SbF_5$). Fluoroantimonic acid is an inorganic compound with the chemical formula $H_2FSbF_6$ (also written $H_2F[SbF_6]$, $2HF \cdot SbF_5$, or simply HF—$SbF_5$).

Carborane acids $H(CXB_{11}Y_5Z_6)$ (X, Y, Z=H, Alk, F, Cl, Br, $CF_3$) are a class of superacids, some of which are estimated to be at least one million times stronger than 100% sulfuric acid in terms of their Hammett acidity function values ($H_0 \leq -18$) and possess computed pKa values well below −20, establishing them as some of the strongest known Brønsted acids. Examples for suitable carborane acids is $H(CHB_{11}Cl_{11})$.

Fluorosulfuric acid (IUPAC name: sulfurofluoridic acid) is the inorganic compound with the chemical formula $HSO_3F$. Triflic acid, also known as trifluoromethanesulfonic acid, TFMS, TFSA, HOTf or TfOH, is a sulfonic acid with the chemical formula $CF_3SO_3H$.

Depending on the acidity of the solvent or the acidity of the reaction mixture, the reaction speed is improved.

In a very preferred embodiment, the method of the present invention comprises the following steps:
 a. Providing sulfur trioxide $SO_3$;
 b. Providing an haloalkane, especially trifluoromethane;

c. Providing a solvent, wherein said solvent does constitute a superacid and/or the combination of said solvent with SO₃ and/or the haloalkane sulfonic acid does give rise to a superacid;
d. Bringing into contact SO₃, haloalkane and the solvent in a high-pressure autoclave or laboratory reactor;
e. Setting a pressure of from 1 to 200 bar;
f. Adding a compound which is able to initialize the reaction between SO₃ and haloalkane at the described reaction conditions;
g. Controlling the temperature of the reaction mixture at 0° C. to 100° C.;
h. Letting react the compounds so that the haloalkane sulfonic acid, especially triflic acid, is formed.

Accordingly, a compound is added which initializes the reaction between SO₃ and the haloalkane at the described reaction conditions. This compound may be provided in pure form or solved in a suitable solvent with the proviso that preferably this solvent again does not constitute a super acid and the combination of said solvent with SO₃ and/or the haloalkane sulfonic acid does not give rise to super acid. If this solvent does not constitute a superacid itself and/or in combination with SO₃ and/or haloalkane sulfonic acid, the amount of said solvent is to be controlled the conditions inside the reactor are still superacid.

Preferably, in cases this compound is added together with the solvent, this solvent is the same as used in the reaction as a whole. If such a compound is added, the initial molar ratio between this compound and SO₃ is in the range of 1:50 to 1:10000, preferably 1:100 to 1:500, particularly 1:150.

The compound added at step f) of the method according to the above preferred embodiment may be a compound being known to initialize the reaction between an haloalkane and SO₃ to form haloalkane sulfonic acid under super acid conditions. Therefore, the compound added at step f) is preferably selected from the group consisting of organic or inorganic peroxides being stable at room temperature, compounds with a heterogeneously or homogenously cleavable bond, stable cations as well as mixtures of two or more of them. Suitable compounds are for example disclosed in EP18174283.4, the content of which is enclosed herein in its entirety.

Especially, preferred, a compound is added according to the following formula (I):

ALK-SO₂—O—O—X            (I)

wherein ALK is a branched or unbranched alkyl group, especially a methyl, ethyl, propyl, butyl, isopropyl, isobutyl group, or a higher alkyl group, and X=hydrogen, zinc, aluminium, an alkali or alkaline earth metal. Higher alkyl group within the meaning of the present invention means an alkyl group with 1 to 10 carbon atoms. Preferably, ALK is methyl, ethyl, propyl, butyl, isopropyl or isobutyl, especially methyl or ethyl, particularly methyl. X is preferably hydrogen, alkali or alkaline earth metal. Particularly, X is hydrogen. Thus, in a very preferred embodiment, the compound added to initialize the reaction between SO₃ and haloalkane is CH₃—SO₂—O—O—H.

Alternatively, the compound added in step f) of the preferred embodiment is an organic peroxoacid which, where appropriate, comprises functional groups. In general, the peroxoacid according to the invention can be described by the formula R—O—O—H. In a preferred embodiment the peroxoacid comprises at least one organic peroxoacid of sulfur, phosphorus, silicon, boron, nitrogen or carbon. Any suitable peroxoacid of said elements can be used. The peroxoacids are typically derived from the corresponding oxoacid of the respective element.

Preferably, the peroxoacid used as catalyst according to the invention comprises a peroxoacid group corresponding to $-E(=X)_m(-YZ)_n-O-O-Z$, wherein E is selected from the group consisting of S, P, Si, B, N and C, wherein X and Y may be the same or different and are selected from the group consisting of O and S, wherein m is an integer of from 0 to 2, wherein n is an integer of from 0 to 2, and wherein Z is H, Li, Na and/or K.

In a preferred embodiment of the invention, the peroxoacid group is selected from the group consisting of —SO₂—O—O—X, —CO—O—O—X, —PO(OH)—O—O—X, PS(OH)—O—O—X, wherein X is H, Li, Na and/or K. Surprisingly, it has been found that said preferred peroxoacids are particularly suitable as catalyst in the preparation of haloalkanesulfonic acids from haloalkanes and sulfur trioxide According to the invention, the organic peroxoacid comprises at least one additional functional group. The additional functional group may particularly be selected from the group consisting of carbon double bonds, carbon triple bonds, aryl groups, heteroaryl groups and functional groups comprising heteroatoms, especially functional groups comprising O, S, N, P, Si, B, Se, Te, F, Cl, Br, I, Mg or Li atoms.

Particularly preferred are aryl groups, halogen atoms, such as F, Cl, Br, I, and siloxane groups. The functional groups, particularly aryl groups, may be further derivatized and may contain further functional groups. Examples of functional groups according to the invention comprise particularly phenyl groups, carbonyl groups, ether groups, thioether groups, thioketone groups and halide groups.

Examples of suitable organic peroxoacids according to the invention are peroxybenzoic acid and trifluoroperacetic acid. Any of the aforementioned examples may be derivatized and/or substituted with side chains, particularly with alkyl groups, aryl groups or halogen atoms.

The organic peroxoacid used as a catalyst according to the invention may be obtainable by a reaction of the corresponding oxoacid with a peroxide. More preferably, the peroxoacid may be obtainable by a reaction of the corresponding oxoacid with hydrogen peroxide or a salt thereof. Without the intention of being bound by theory, the reaction of an oxoacid with hydrogen peroxide can for example be described by

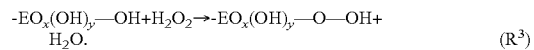

-EO_x(OH)_y—OH+H₂O₂→-EO_x(OH)_y—O—OH+ H₂O.            (R³)

If such an organic peroxoacid is used as compound, it is only suitable if it does not give rise to superacid conditions in the reactor at which the reaction takes place. This may be controlled by selecting the compound carefully or by using it in only small amounts.

In a further preferred embodiment, the compound is an inorganic peroxoacid or a salt thereof, wherein the peroxoacid is stable at room temperature. Stability at room temperature is particularly to be understood as stability in a reaction solvent comprising sulfur trioxide and an haloalkane, especially trifluoromethane. This solvent may be sulfuric acid. The peroxoacid according to the invention must be stable enough in order to act as catalyst in the production of haloalkanesulfonic acids and not to decompose. Said decomposition may particularly take place by the release of reactive oxygen species such as superoxide anions ($O_2^-$). In this sense, stability of the peroxoacid catalysts of the present invention for example means the absence of the release of reactive oxygen species such as superoxide anions.

In a preferred embodiment the peroxoacid comprises at least one peroxoacid of boron, silicon, phosphorus, carbon, nitrogen or sulfur. Any suitable peroxoacid of said elements can be used. The peroxoacids are typically derived from the corresponding oxoacid of the respective element.

Preferably, the peroxoacid used as a catalyst according to the invention is obtainable by a reaction of the corresponding oxoacid with a peroxide. More preferably, the peroxoacid is obtainable by a reaction of the corresponding oxoacid with hydrogen peroxide. Without the intention of being bound by theory, the reaction of an oxoacid with hydrogen peroxide can for example be described by

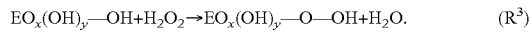

$$EO_x(OH)_y—OH+H_2O_2 \rightarrow EO_x(OH)_y—O—OH+H_2O. \quad (R^3)$$

In a preferred embodiment, the peroxoacid used according to the invention comprises a polyprotic acid. Particularly, the peroxoacid may consist of one or more polyprotic acids. Said polyprotic peroxoacid comprises one or more peroxy groups, which can be described by —O—O—X, wherein X may be hydrogen and/or an alkaline and/or alkaline-earth metal. More preferably X is hydrogen, lithium, sodium and/or potassium. Most preferably, X is hydrogen.

Preferably, if a polyprotic acid is used, the peroxoacid comprises one or more hydroxyl groups in addition to the one or more peroxy groups. Said hydroxyl groups may be present in form of a salt, i.e., the groups can be described by —O—X, wherein X may be hydrogen, an alkaline metal and/or an alkaline-earth metal. Most preferably X is hydrogen. The replacement of hydrogen with an alkaline-(earth) metal, however, may be particularly necessary to stabilize the peroxoacid as required by the invention.

In a preferred embodiment of the invention, the reaction product of phosphoric acid ($H_3PO_4$) with hydrogen peroxide, the reaction product of boric acid ($H_3BO_3$) with hydrogen peroxide and/or potassium peroxomonosulfate ($KHSO_5$) is used as stable inorganic peroxoacid according to the invention. Surprisingly, it has been found that said preferred peroxoacids are particularly suitable as catalyst in the preparation of haloalkanesulfonic acids from haloalkanes and sulfur trioxide.

If such an inorganic peroxoacid is used as compound, it is only suitable if it does not give rise to superacid conditions in the reactor at which the reaction takes place. This may be controlled by selecting the compound carefully or by using it in only small amounts.

In another embodiment, the compound is a compound comprising a heterolytically cleavable bond between an atom selected from the group consisting of nitrogen, phosphor sulfon oxygen and an atom selected from the group consisting of nitrogen, phosphor and sulfur.

A heterolytically cleavable bond in the sense of the present invention is especially a chemical bond —X—Y— between two atoms X and Y, which may be broken in such a way that the remaining fragments are not two radicals with unpaired electrons. Particularly, the electrons of the bond are unequally partitioned between atoms X and Y upon cleavage of the bond. The atoms X and Y of the heterolytically cleavable bond may additionally be bound to the same or different radicals. The bond between X and Y may be polarized. Polarization of the bond may enable or favor heterolytical cleavage of the bond. Polarization may, for example, be accomplished by choosing two different elements for atoms X and Y, especially elements with different electronegativities. Polarization of the bond may also be accomplished by choosing different radicals, to which atoms X and Y are additionally bound. These measures may be combined, when X and Y are different and bound to at least two different additional radicals. In principal, any compound comprising heterolytically cleavable bonds in the aforementioned sense can be employed according to the invention. Such compounds are cheaply available from commercial distributors.

In a preferred embodiment the heterolytically cleavable bond is a single bond or a double bond. Alternatively, the heterolytically cleavable bond may also be a triple bond. Particularly preferred are single bonds. If a double bond is cleaved, it could be that the bond is cleaved completely. Within the scope of the present invention it is also that a single bond remains and only one bond cleaves heterolytically. The same is of course true for the triple bond.

The bond is preferably heterolytically cleavable under acidic conditions. Particularly preferred are bonds, which are heterolytically cleavable under superacid conditions.

Heterolytic cleavage of the bond of the inventive catalyst preferably generates a cation and/or an anion. If the cleavage of the bond is catalyzed by an acid, particularly $H^+$, the anion may formally react with the acid upon cleavage. In this case, only a cation and a neutral compound are generated.

The compound, which is used as catalyst according to the invention, is preferably selected from the group consisting of $R^1$—N—N—$R^2$, $R^1$—N—O—$R^2$, $R^1$—N—P—$R^2$, $R^1$—S—N—$R^2$, $R^1$—P—P—$R^2$, $R^1$—P—O—$R^2$, $R^1$—S—P—$R^2$, $R^1$—S—O—$R^2$ and $R^1$—S—S—$R^2$, wherein $R^1$ and $R^2$ may be the same or different and are selected from the group consisting of hydrogen, organic radicals and inorganic radicals. Particularly if the catalyst is chosen from $R^1$—N—N—$R^2$, $R^1$—P—P—$R^2$ and $R^1$—S—S—$R^1$, $R^1$ and $R^2$ may be different in order to polarize the bond and favor heterolytic cleavage of the bond.

In a preferred embodiment $R^1$ and/or $R^2$ are selected from the group consisting of -E(=X)$_m$(—YZ)$_n$, -E(=X)$_m$(—YZ)$_n$—$R^3$, -E(=X)$_m$(—YZ)$_n$—$R^3R^4$ and -E(=X)$_m$(—YZ)$_n$—$R^3R^4R^5$, wherein $R^3$, $R^4$ and $R^5$ are each directly bonded to E, may be the same or different and are selected from the group consisting of hydrogen, organic radicals and inorganic radicals, wherein E is selected from the group consisting of S, P, Si, B, N and C, wherein X and Y may be the same or different and are selected from the group consisting of O and S, wherein m is an integer of from 0 to 2, wherein n is an integer of from 0 to 3 and wherein Z is H, Li, Na and/or K.

In these preferred embodiments, the atom X and/or the atom Y, which form the heterolytically cleavable bond, may each be directly bound to an atom E selected from S, P, Si, B, N and C. Depending on the valence of atom E, said atom may additionally be bound to up to three further radicals $R^3$, $R^4$ and $R^5$. The place of the radicals $R^3$, $R^4$ and $R^5$ can alternatively be filled with oxygen or sulphur atoms, which are double bonded to E, or groups YZ, which primarily correspond to OH and SH groups and their derivates. The inventive catalyst compound may therefore, for example, be a derivate of an oxoacid of sulfur, phosphorus, silicon, boron, nitrogen or carbon.

In a particularly preferred embodiment of the invention, $R^1$ and/or $R^2$ are selected from the group consisting of —SO$_2$—$R^3$, —SO$_2$OH, —CO—$R^3$, —PO(OH)—$R^3$, —PS(OH)—$R^3$, —Si(OH)$_3$, —Si(OH)$_2$—$R^3$, —SiH$_3$ and —SiH$_2$—$R^3$.

Each of the aforementioned radicals $R^1$, $R^2$, $R^3$, $R^4$ and $R^5$ may preferably be individually selected from the group consisting of alkyl radicals, alkyl radicals substituted with one or more functional groups, siloxane radicals or any other suitable inorganic or organic radical.

Preferred alkyl radicals are branched or unbranched alkyl radicals with a carbon number of 1 to 20, especially 1 to 10, particularly methyl, ethyl, propyl, butyl, isopropyl, isobutyl or higher alkyl radicals.

The aforementioned additional functional groups may particularly be selected from the group consisting of carbon double bonds, carbon triple bonds, aryl groups, heteroaryl groups and functional groups comprising heteroatoms, especially functional groups comprising O, S, N, P, Si, B, Se, Te, F, Cl, Br, I, Mg or Li atoms.

Particularly preferred are aryl groups, halogen atoms, such as F, Cl, Br, I, and siloxane groups. The functional groups, particularly aryl groups, may be further derivatized and may contain further functional groups. Examples of functional groups according to the invention comprise particularly phenyl groups, carbonyl groups, ether groups, thioether groups, thioketone groups and halide groups.

In yet another preferred embodiment, the compound added in step f) of the preferred method is a cation being stable under super acid conditions. If the cation is stable, stability in this context means that it is able to react with the haloalkane but does not decompose within 24 h at room temperature (20° C.), i.e. the half-life time $t_{1/2}$ at room temperature is at least 24 h, preferably at least 30 h, especially at least 48 h.

Stable cations are formed prior to their use, i.e. prior to their addition into the reactor in which the reaction between haloalkane and sulfur trioxide takes place. Preferably, one type of cation is used alone and not together with another type of cation.

Alternatively, the cation is produced in situ during the production of the haloalkane sulfonic acid. In such cases a compound is added to the reaction and the cation is formed according to the above shown reaction ($R^2$). Suitable compounds to be used are halogens, especially $I_2$ and $Br_2$, inter halogen compounds, especially I—Br, or solid elements of the $15^{th}$ or $16^{th}$ group of the periodic table of elements, especially S, Se, Te, P, As, Sb.

If halogens or interhalogens are used as compounds, the bond between the halogens breaks heterolytically. Iodine would thus react to HI and $I^+$, bromine to HBr and $Br^+$, and the interhalogen either to HI and $Br^+$ or to HBr and $I^+$. The reactive cation would be $I^+$ or $Br^+$, which is formed in situ, and afterwards reacts with the haloalkane to the haloalkane cation as schematically shown above in ($R^1$).

If solid elements of the $15^{th}$ or $16^{th}$ group of the periodic table are used, they may form oligomeric or polymeric cationic compounds, i.e., sulfur will form an oligomer $Sn—S^+$, wherein n may for example be in the range of from 0 to 10, preferably from 2 to 10, or in another range. Said $Sn—S^+$ would be the reactive compound. Similar compounds may also occur with the other elements. Alternatively, they can form cations without polymerisation/oligomerisation. To sum up all possible cations of S, Se, Te, As, Sb and P, they are summarized with $S+$, $Se^+$, $Te^+$, $As^+$, $Sb^+$, and $P^+$ respectively. Additionally, also Silicon may be added to the reaction solution forming $Si^+$ as cation.

The present invention is exemplarily further disclosed in the following example:

Preparation of the Initiator-Solution:

100 ml triflic acid were cooled with an ice baths and 20 ml of hydrogen peroxide were added dropwise under extensive cooling.

In a 1 gallon (3.75 L) high pressure laboratory reactor equipped with a gas-injection-stirrer 400 g of pure sulfur trioxide ($SO_3$) were dissolved in 1 liter of fluorosulfonic acid as solvent. In the next step an excess of liquified fluoroform ($CHF_3$) was added and the temperature of the reaction mixture was set to 50° C. Afterwards the initiator-solution was added dropwise. The reaction is finished after 12 h and was worked up by adding water to quench the unreacted sulfur trioxide. The purification using a 2-step distillation yields to the pure product (82%).

The invention claimed is:

1. A method for producing a haloalkane sulfonic acid, comprising the steps of:
    a) contacting sulfur trioxide ($SO_3$—), a haloalkane, and compound which is able to initialize the reaction between sulfur trioxide ($SO_3$) and haloalkane with each other in the presence of a solvent,
    wherein at least one of:
    i) said solvent is a superacid; and
    ii) the combination of said solvent with one or more of sulfur trioxide ($SO_3$) and the haloalkane sulfonic acid gives rise to a superacid; and
    wherein the solvent is not $H_2SO_4$.

2. The method according to claim 1, wherein a superacid is an acid having a pKa value of less than −3.

3. The method according to claim 1, wherein the haloalkane is selected from the group consisting of trifluoromethane, trifluoroethane, trifluoropropane, trifluorobutane and trifluoropentane.

4. The method according to claim 1, wherein sulfur trioxide ($SO_3$) and haloalkane are contacted with each other at a temperature within a range of from one of:
    a) 0° C. to 100° C.,
    b) 15° C. to 80° C.,
    c) 20° C. to 70° C., and
    d) 35° C. to 60° C.

5. The method according to claim 1, wherein the solvent is a liquid under the conditions at which the sulfur trioxide ($SO_3$) and the haloalkane are contacted with each other.

6. The method according to claim 1, wherein the solvent is selected from the group consisting of one or more of fluoroantimonic acid, carborane acid, magic acid, fluorosulfuric acid, hydrogen fluoride, and triflic acid.

7. The method according to claim 1, wherein the solvent is not Marshall's acid or Caro's acid.

8. The method according to claim 1, further comprising the following steps:
    a) providing sulfur trioxide ($SO_3$);
    b) providing a haloalkane;
    c) providing a solvent, wherein said solvent is a superacid or the combination of said solvent with one or more of the sulfur trioxide ($SO_3$) and the haloalkane sulfonic acid gives rise to a superacid;
    d) bringing into contact sulfur trioxide ($SO_3$), haloalkane, and the solvent in a high-pressure autoclave or laboratory reactor;
    e) setting a pressure of from 1 to 200 bar;
    f) adding a compound which is able to initialize the reaction between sulfur trioxide ($SO_3$) and haloalkane;
    g) controlling the temperature of the reaction mixture between about 0° C. to 100° C.; and
    h) forming the haloalkane sulfonic acid.

9. The method according to claim 8, wherein the compound added at step f) is a compound selected from the group consisting of one or more of (i) organic and inorganic peroxides being stable at room temperature, (ii) compounds with a heterolytically or homogenously cleavable bond, as well as mixtures thereof.

10. The method according to claim 9, wherein the compound of step f) is ALK-$SO_2$—O—O—X, wherein ALK is a branched or unbranched alkyl group, or a higher alkyl group, and X is a hydrogen, zinc, aluminium, or an alkali or alkaline earth metal.

11. The method of claim 3, wherein the haloalkane is trifluoromethane.

12. The method of claim 6, wherein the solvent is selected from the group consisting of two or more of fluoroantimonic acid, carborane acid, magic acid, fluorosulfuric acid, hydrogen fluoride, and triflic acid.

13. The method of claim 8, wherein the haloalkane is trifluoromethane.

14. The method of claim 8, wherein the haloalkane sulfonic acid is triflic acid.

15. The method of claim 10, wherein ALK is selected from the group consisting of methyl, ethyl, propyl, butyl, isopropyl, and isobutyl.

16. The method of claim 15, wherein ALK is methyl.

17. The method of claim 10, wherein X is hydrogen.

18. The method of claim 10, wherein the compound of step f) is $CH_3-SO_2-O-O-H$.

* * * * *